US007884226B2

(12) United States Patent
Nidam et al.

(10) Patent No.: US 7,884,226 B2
(45) Date of Patent: Feb. 8, 2011

(54) PURIFICATION OF ROSUVATATIN INTERMEDIATE BY THIN FILM EVAPORATION AND CHEMICAL METHOD

(75) Inventors: Tamar Nidam, Yehud (IL); Omer Malachi, Rehovot (IL); Irena Veinberg, Rehovot (IL); Valerie Niddam-Hildesheim, Kadima (IL); Vinod Kumar Kansal, Haryana (IN); Harish Ranjan, New Delhi (IN); Appu Ekambaram Ponnuswamy, Andhra Pradesh State (IN); Sunil Rokad, Gujrat (IN); Surat Kiran, Andhra pradesh (IN); Debashish Das, Delhi (IN)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 245 days.

(21) Appl. No.: 12/218,403

(22) Filed: Jul. 14, 2008

(65) Prior Publication Data

US 2009/0099383 A1 Apr. 16, 2009

Related U.S. Application Data

(60) Provisional application No. 60/959,383, filed on Jul. 12, 2007, provisional application No. 60/962,879, filed on Jul. 31, 2007, provisional application No. 61/069,098, filed on Mar. 11, 2008, provisional application No. 60/997,446, filed on Oct. 2, 2007, provisional application No. 61/126,638, filed on May 5, 2008.

(51) Int. Cl.
   C07F 9/02 (2006.01)
(52) U.S. Cl. ...................... 558/149; 558/146
(58) Field of Classification Search .................. 558/149, 558/146
See application file for complete search history.

(56) References Cited

U.S. PATENT DOCUMENTS

| | | | |
|---|---|---|---|
| 5,260,440 A | 11/1993 | Hirai et al. | |
| 5,354,879 A | 10/1994 | Konoike et al. | |
| 5,717,124 A | 2/1998 | Harada et al. | |
| RE37,314 E | 8/2001 | Hirai et al. | |
| 6,777,552 B2 | 8/2004 | Niddam-Hildesheim et al. | |
| 6,909,003 B2 | 6/2005 | Storz | |
| 7,208,623 B2 | 4/2007 | Sedelmeier et al. | |
| 7,371,865 B2 | 5/2008 | Acemoglu et al. | |
| 2005/0080134 A1 | 4/2005 | Niddam-Hildesheim et al. | |
| 2006/0116391 A1 | 6/2006 | Horbury et al. | |
| 2006/0149065 A1 | 7/2006 | Kumar et al. | |
| 2007/0099994 A1 | 5/2007 | Niddam-Hildesheim et al. | |
| 2007/0167625 A1 | 7/2007 | Balanov et al. | |
| 2007/0191318 A1 | 8/2007 | Kumar et al. | |
| 2007/0255060 A1 | 11/2007 | Okada et al. | |
| 2008/0091014 A1 | 4/2008 | Huang | |
| 2009/0069563 A1 | 3/2009 | Niddam-Hildesheim et al. | |

FOREIGN PATENT DOCUMENTS

| | | |
|---|---|---|
| CN | 1807417 | 7/2006 |
| CN | 1821242 | 8/2006 |
| CN | 1307187 C | 3/2007 |
| CN | 1958593 | 5/2007 |
| CZ | 298330 | 8/2007 |
| EP | 0 554 455 | 8/1993 |
| EP | 0 850 902 | 7/1998 |
| WO | WO 00/49014 A | 8/2000 |
| WO | WO 03/087112 | 10/2003 |
| WO | WO 03/087112 A1 * | 10/2003 |
| WO | WO 03/097614 A | 11/2003 |
| WO | WO 2006136407 | 12/2006 |
| WO | WO 2006136408 | 12/2006 |
| WO | WO 2007/069264 | 6/2007 |
| WO | WO 2007099561 | 9/2007 |
| WO | WO 2008/044243 | 4/2008 |

OTHER PUBLICATIONS

Lipid Research Clinics Program, "The Lipid Research Clinics Coronary Primary Prevention Trial Results: I. Reduction in Incidence Of Coronary Heart Disease", *J.A.M.A.*, 1984, 351-74, vol. 251, No. 3.
Scandinavian Simvastatin Survival Study Group, "Randomised Trial Of Cholesterol Lowering In 4444 Patients With Coronary Heart Disease: The Scandinavian Survival Study (4s)", *The Lancet*, 1994, pp. 1383-1389, vol. 344.
Watanabe, Masamichi et al., "Synthesis and biological activity of methanesulfonamide pyrimidine- and N-methanesulfonyl pyrrole-substituted 3,5-dihydroxy-6-heptenoates, a novel series of HMG-CoA reductase inhibitors," *Bioorganic & Medicinal Chemistry*, 5(2), pp. 437-444, 1997.
Witztum, "Chapter 36: Drugs Used In The Treatment Of Hyperlipoproteinemias", *Goodman & Gilman's The Pharmacological Basis Of Therapeutics*, 9th ed., 1996, p. 879.
European Office Action, dated Sep. 21, 2010, from corresponding European Patent Application No. 08 794 498.9.
"Thin Film Evaporator Systems", Pfaudler Reactor Systems, 2010, http://www.pfaudler.com/thin_film_evaporator_systems.php.

* cited by examiner

*Primary Examiner*—Rei-tsang Shiao
(74) *Attorney, Agent, or Firm*—Kenyon & Kenyon LLP

(57) ABSTRACT

Provided are processes for the purification of a pure rosuvastatin intermediate by thin film evaporation and chemical method, and conversion of the intermediate to rosuvastatin or salts thereof.

31 Claims, 7 Drawing Sheets

PURIFICATION OF ROSUVATATIN INTERMEDIATE BY THIN FILM EVAPORATION AND CHEMICAL METHOD

CROSS-REFERENCE TO RELATED APPLICATIONS

The present invention claims the benefit of the following U.S. Provisional Patent Application Nos. 60/959,383, filed Jul. 12, 2007; 60/962,879, filed Jul. 31, 2007; and 61/069,098, filed Mar. 11, 2008. The contents of these applications are incorporated herein by reference and claims the benefit of U.S. Provisional Patent Application Nos. 60/997,446, filed Oct. 2, 2007, and 61/126,638, filed May 5, 2008.

FIELD OF THE INVENTION

The invention is directed to processes for purifying 19TBPO, an intermediate of rosuvastatin.

BACKGROUND OF THE INVENTION

Complications of cardiovascular disease, such as myocardial infarction, stroke, and peripheral vascular disease account for half of all deaths in the United States. A high level of low density lipoprotein (LDL) in the bloodstream has been linked to the formation of coronary lesions which obstruct the flow of blood and promote thrombosis. (See Goodman and Gilman, *The Pharmacological Basis of Therapeutics*, 9$^{th}$ ed., p. 879 (1996)). Reducing plasma LDL levels has been shown to reduce the risk of clinical events in patients with cardiovascular disease and in patients who are free of cardiovascular disease but who have hypercholesterolemia. (Scandinavian Simvastatin Survival Study Group, 1994; Lipid Research Clinics Program, 1984a, 1984b.)

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin.

The mechanism of action of statin drugs has been elucidated in some detail. The statin drugs disrupt the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, HMG-CoA reductase inhibition leads to a reduction in the rate of formation of cholesterol in the liver. Decreased production of cholesterol causes an increase in the number of LDL receptors and corresponding reduction in the concentration of LDL particles in the bloodstream. Reduction in the LDL level in the bloodstream reduces the risk of coronary artery disease. (J.A.M.A. 1984; 251: 351-74).

Currently available statins include: lovastatin, simvastatin, pravastatin, fluvastatin, cerivastatin and atorvastatin, which are administered in their lactone form, as sodium salts, or as calcium salts.

Rosuvastatin (7-[4-(4-fluorophenyl)-6-isopropyl-2-(N-methyl-N-methylsulfonylamino) pyrimidin-5-yl]-(3R,5S)-dihydroxy-(E)-6-heptenoic acid) calcium, an HMG-CoA reductase inhibitor, can lower LDL-cholesterol and triglycerides levels more effectively than first generation statin drugs. Rosuvastatin calcium has the following chemical formula:

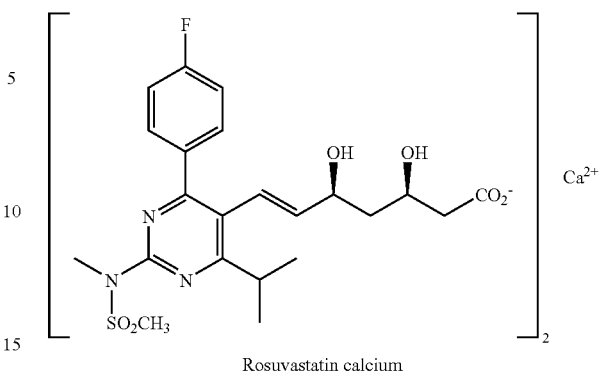

Rosuvastatin calcium

A number of processes for the preparation of rosuvastatin and salts thereof are disclosed. Rosuvastatin calcium, intermediates of rosuvastatin, and their preparation are disclosed in U.S. Pat. No. 5,260,440, herein the '440 patent. WO 03/097614 discloses the synthesis of rosuvastatin from the late intermediate methyl (3R)-3-(tert-butyldimethylsilyloxy)-5-oxo-6-triphenyl-phosphoranylidene hexanate, an intermediate disclosed in the '440 patent. WO 03/087112 discloses the synthesis of rosuvastatin from a different intermediate, t-butyl (3R)-3-(t-butyldimethylsilyloxy)-6-dimethoxyphosphinyl-5-oxohexanate. WO/0049014 discloses the synthesis of rosuvastatin using intermediates with other side chains via a Wittig reaction. EP 850,902 discloses the removal of triphenylphosphine derivatives in mixtures.

Other intermediates and their preparation are also described in, e.g. U.S. Pat. No. 5,354,879, which discloses the purification by column chromatography of the intermediate methyl-(3R)-3-(tert-butyldimethylsilyloxy)-6-dimethoxyphosphinyl-5-oxohexanoate, which is obtained as an oily residue. This intermediate and its preparation are also mentioned in U.S. Pat. No. 5,717,124.

WO 03/087112 discloses a process for the preparation of t-butyl (3R)-3-(t-butyldimethylsilyloxy)-6-dimethoxyphosphinyl-5-oxohexanoate, which yields a product having a purity of 99.5%, obtained by silica gel column chromatography.

Like any synthetic compound, rosuvastatin calcium can contain extraneous compounds or impurities that can come from many sources. These can include unreacted starting materials, by-products of the reaction, products of side reactions, or degradation products. Impurities in rosuvastatin or any active pharmaceutical ingredient (API) are undesirable, and, in extreme cases, might even be harmful to a patient being treated with a dosage form of the API in which a sufficient amount of impurities is present.

There remains a need in the art for cost effective and industrial scale preparation processes of preparing rosuvastatin intermediates.

SUMMARY OF THE INVENTION

The present invention provides a process for the purification of the rosuvastatin intermediate t-butyl (3R)-3-(t-butyldimethylsilyloxy)-6-dimethoxyphosphinyl-5-oxohexanoate (19TBPO) of the following formula

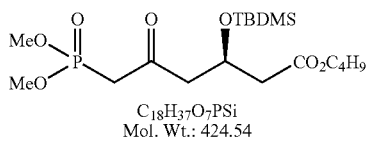

C₁₈H₃₇O₇PSi
Mol. Wt.: 424.54
19TBPO by thin film evaporation.

The present invention provides a process for the purification of the rosuvastatin intermediate t-butyl (3R)-3-(t-butyldimethylsilyloxy)-6-dimethoxyphosphinyl-5-oxohexanoate (19TBPO) of the following formula

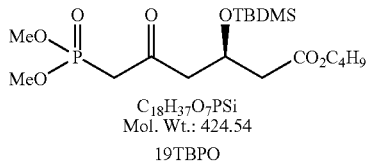

C₁₈H₃₇O₇PSi
Mol. Wt.: 424.54
19TBPO by chemical purification method.

The present invention provides a process for purifying 19TBPO and converting the purified 19TBPO to rosuvastatin or a pharmaceutically acceptable salt thereof.

In one embodiment the present invention provides a process for purifying 19TBPO comprising combining composition containing 19TBPO with basic and/or oxidizing agents, and then extracting the 19TBPO into a water immiscible organic solvent.

In one embodiment the present invention provides a compound 19-TBPO-Eliminate-1 of the following formula:

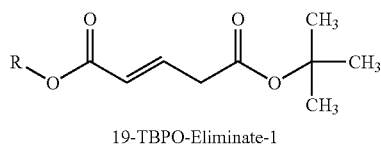

19-TBPO-Eliminate-1 wherein R is methyl, ethyl

In one embodiment the present invention provides a compound 19-TBPO-Eliminate-2 of the following formula:

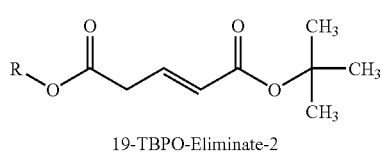

19-TBPO-Eliminate-2 wherein R is methyl, ethyl.

In one embodiment the present invention provides a compound 19-TBPO-cyclic of the following formula:

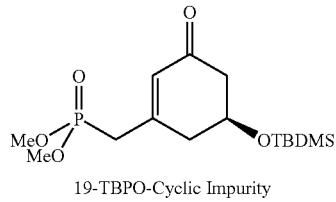

19-TBPO-Cyclic Impurity

In one embodiment the present invention provides a process for preparing 19-TBPO cyclic impurity, comprising the steps of:
a) preparing a mixture of a solvent and dimethylmethyl phosphonate; at a temperature of about −10° C. to about −100° C. to achieve a reaction mixture;
b) combining base with the reaction mixture to obtain a salt.

In one embodiment the present invention provides a process for preparing 19-TBPO cyclic impurity, comprising the steps of:
a) preparing a mixture of a solvent and dimethylmethyl phosphonate; at a temperature of about −10° C. to about −100° C. to achieve a reaction mixture;
b) combining base with the reaction mixture to obtain a salt;
c) adding diethyl tert-butyldimethylsilyloxy glutarate to achieve the Cyclic Impurity;
d) recovering the cyclic impurity.

In an embodiment, the present invention provides pure 19TBPO having a total purity of above 87% area as measured by GC method.

DETAILED DESCRIPTION OF THE INVENTION

Figure 1:
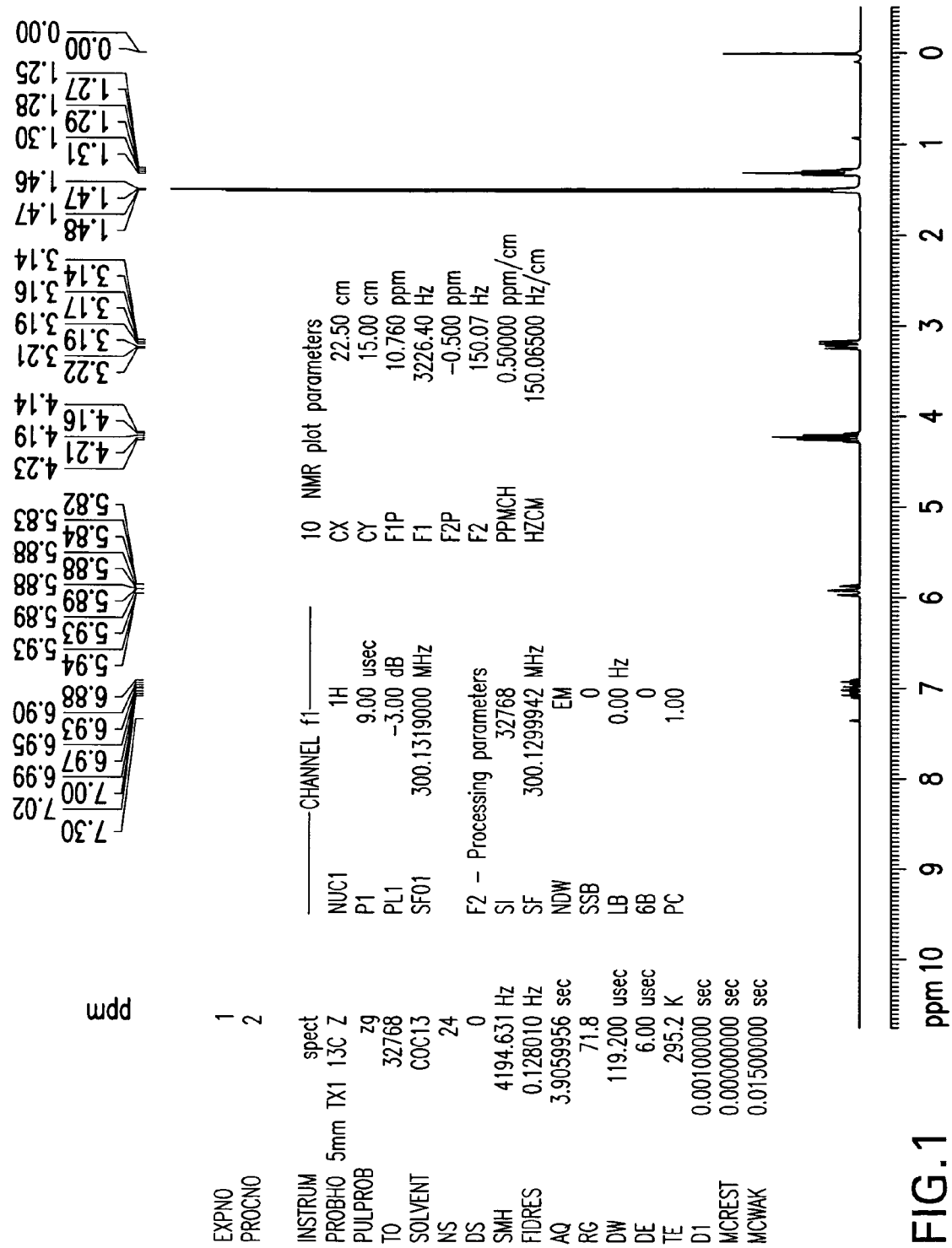
FIG. 1 shows a ¹H-NMR for a mixture of 19TBPO-Eliminate-1 and 19TPO-Eliminate-2.
Figure 2:
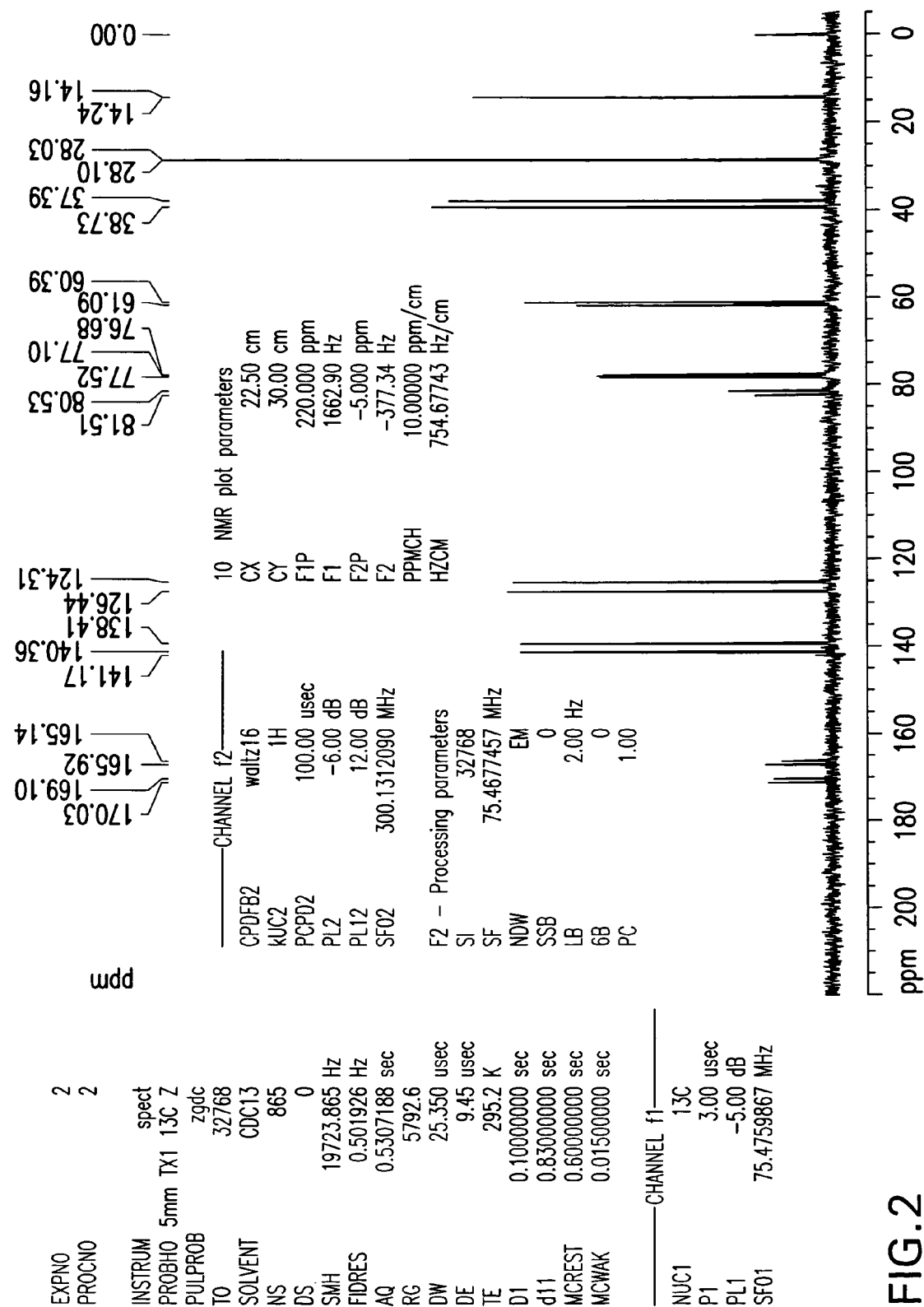
FIG. 2 shows a ¹³C NMR for a mixture of 19TBPO-Eliminate-1 and 19TPO-Eliminate-2.
Figure 3:
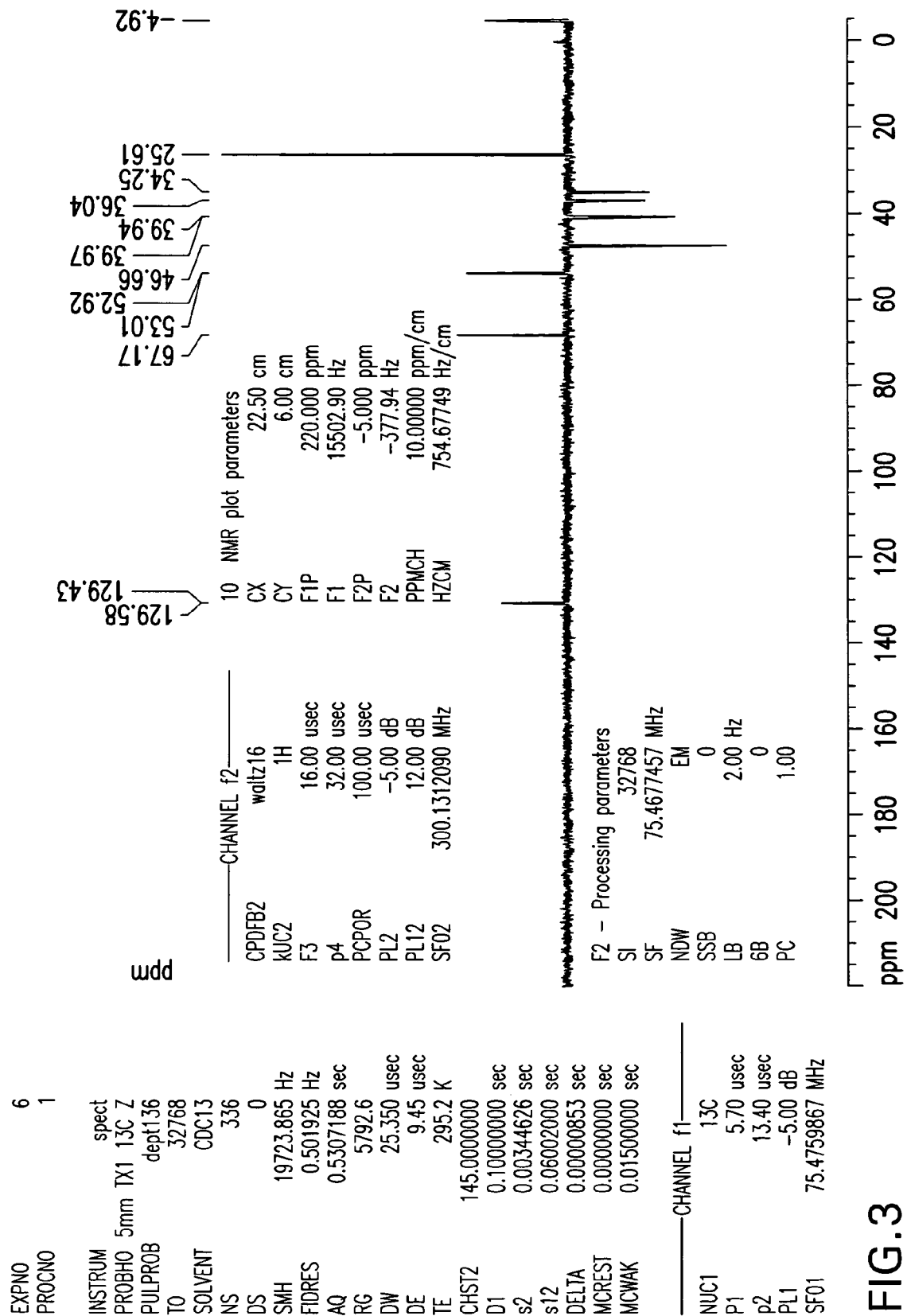
FIG. 3 shows a ¹³C NMR for a mixture of 19TBPO-Eliminate-1 and 19TPO-Eliminate-2.
Figure 4:
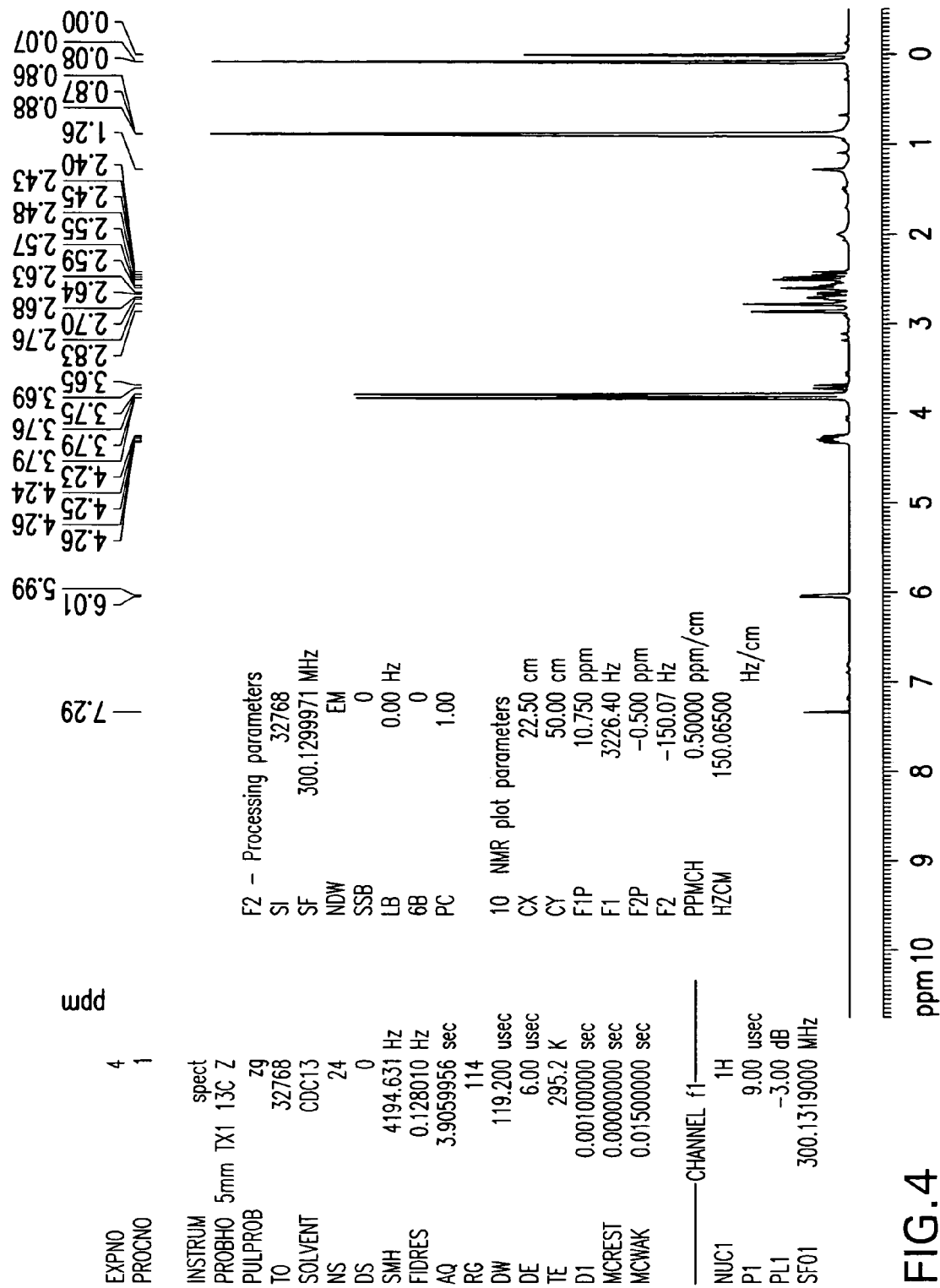
FIG. 4 shows a ¹H-NMR for a 19-TBPO-cyclic impurity.
Figure 5:
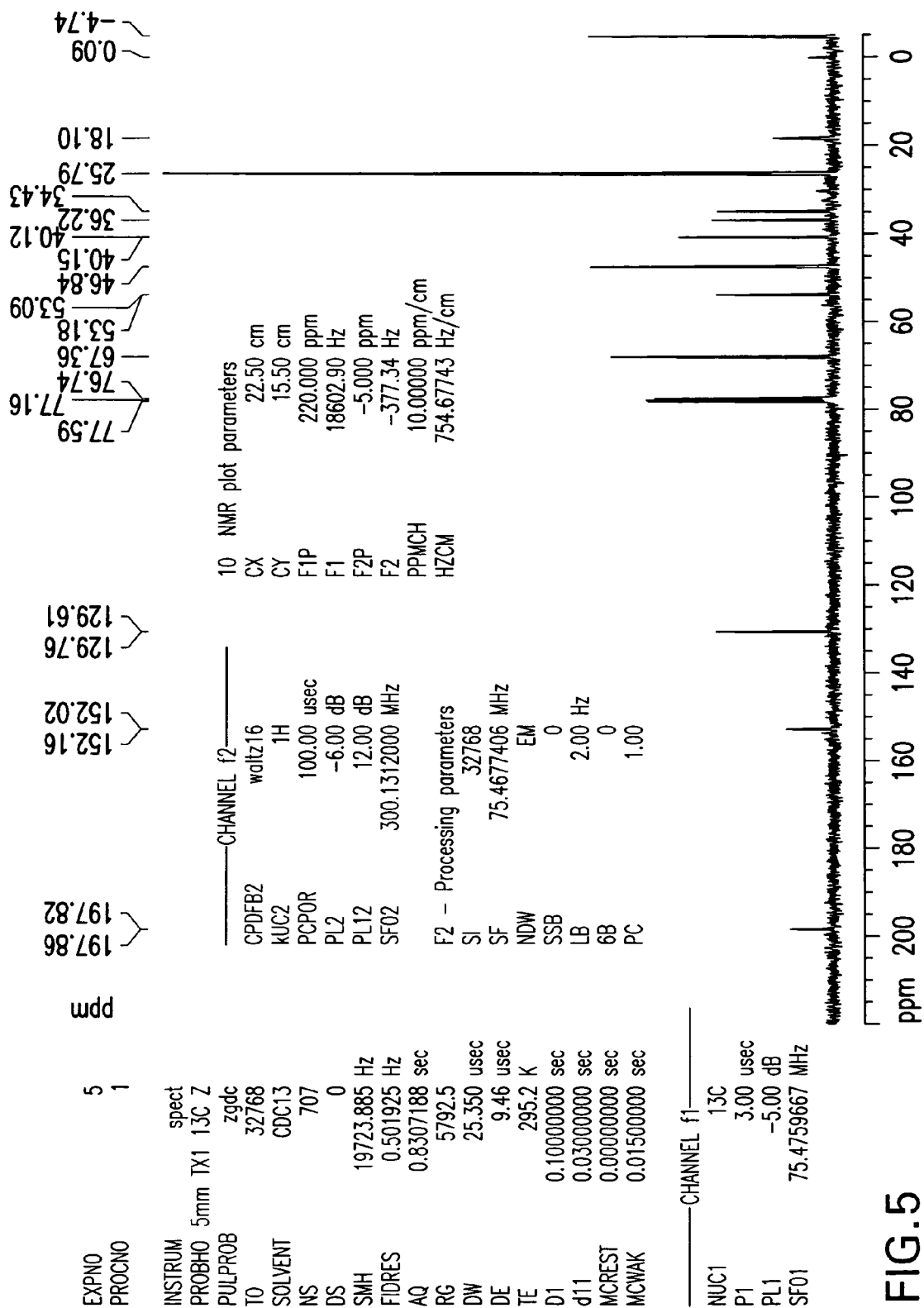
FIG. 5 shows a ¹³C-NMR for a 19-TBPO-cyclic impurity.
Figure 6:
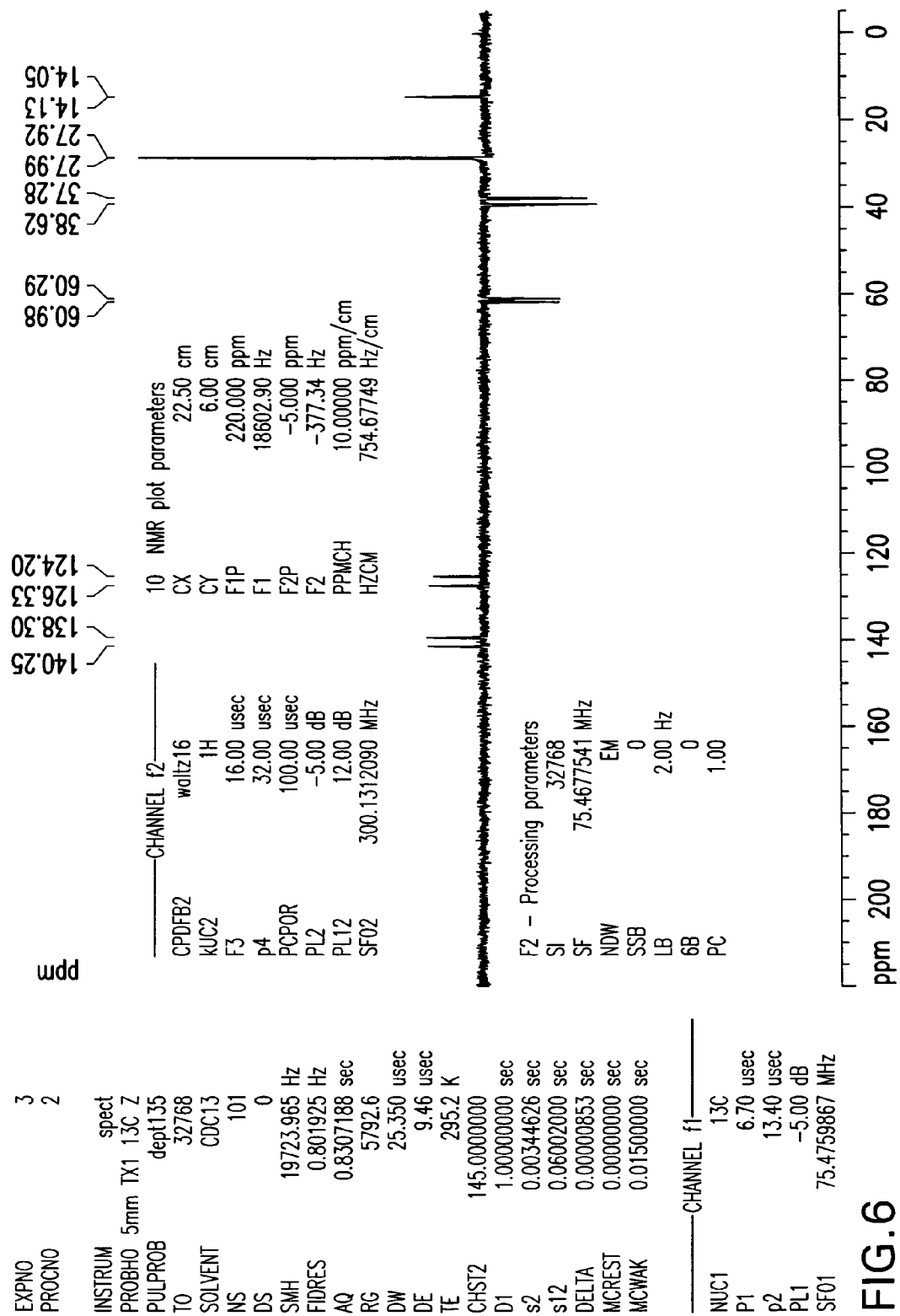
FIG. 6 shows a ¹³C-NMR for a 19TBPO-cyclic impurity.
Figure 7:
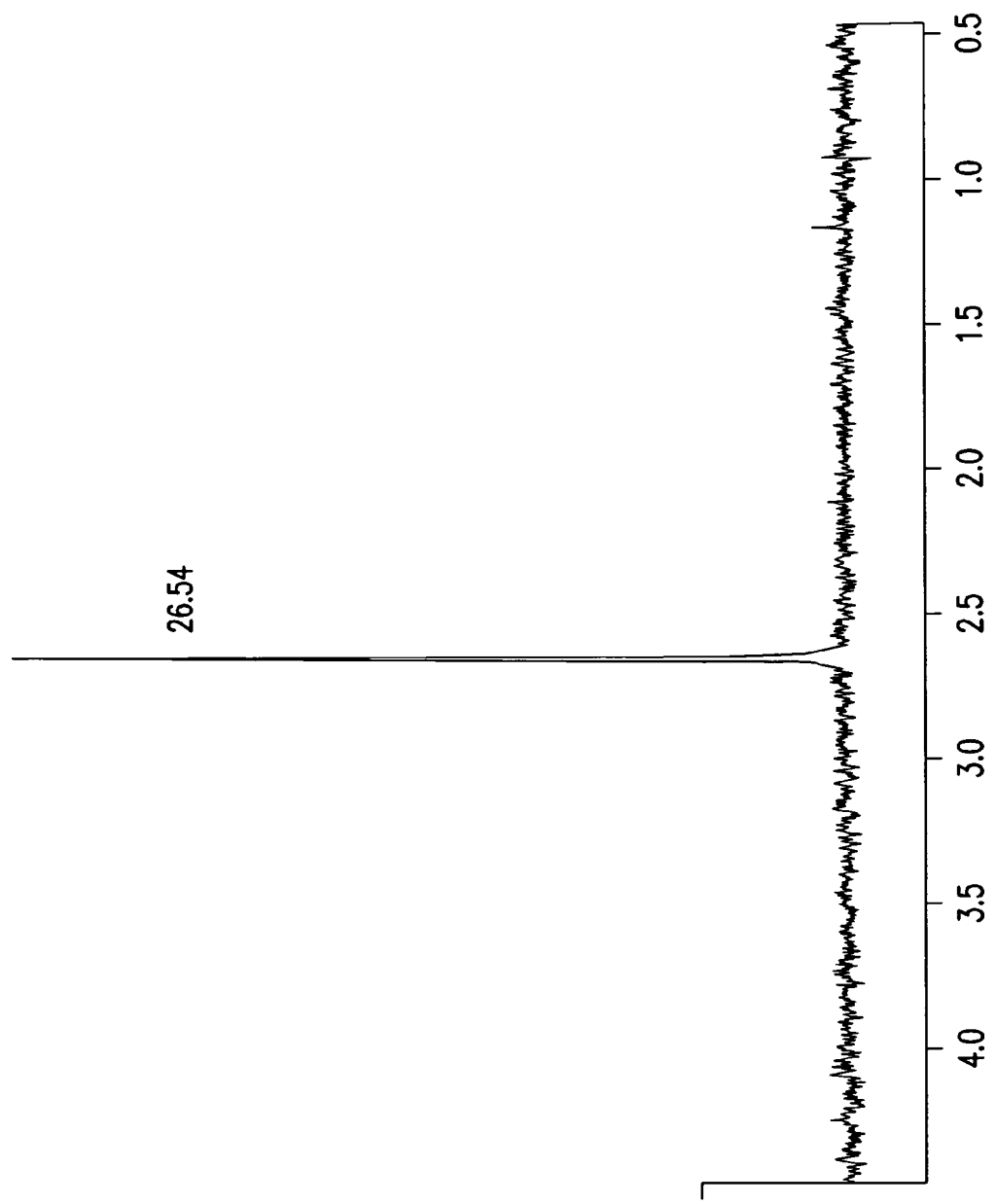
FIG. 7 shows a ³¹P-NMR for a 19TBPO-cyclic impurity.

As used herein, the term "room temperature (RT)" refers to a temperature of about 15° C. to about 30° C.

The intermediate tert-butyl-3R-tert-butyldimethylsilyloxy-6-dimethoxyphosphinyl-5-oxohexanoate, denominated "19TBPO", of the following structure

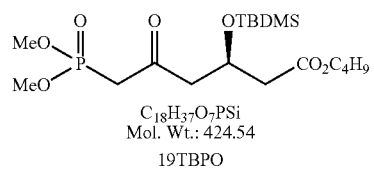

C₁₈H₃₇O₇PSi
Mol. Wt.: 424.54
19TBPO is a key intermediate in the preparation of Rosuvastatin calcium. This intermediate can be produced according to the process described in WO 03/087112, which process is incorporated herein by reference. The process described in WO 03/087112 comprises combining DMMP with THF and BuLi; and adding methyl tert-butyl-3R-tert-butyldimethylsilyloxy-glutarate ("MBSG"). The intermediate 19TBPO however is a transparent to yellowish oil that cannot be purified by conventional scalable methods. One of the feasible ways to achieve this might be distillation methods like conventional vacuum distillation etc.

Further, 19TBPO decomposes at a temperature greater than 100° C., and therefore cannot be purified by conventional distillation, which is another method of purifying oily compounds. Removing the impurities by conventional distillation without causing decomposition would require maintaining 19TBPO under sufficiently low pressure and high temperature. These requirements render conventional distillation methods inappropriate for the purification of large scale quantities of 19TBPO, and therefore conventional distillation or conventional vacuum distillation of 19TBPO is not industrially applicable.

The present invention provides purification methods for preparation of highly pure 19TBPO without degrading 19TBPO.

In one embodiment, the present invention provides 19TBPO with a total purity of above about 87% area as measured by GC method, preferably at least about 90% area as measured by GC method, more preferably at least about 95% area as measured by GC method, even more preferably the purity is at least about 98% area as measured by GC method.

Also provided is 19TBPO having an amount of 19-TBPO-Eliminate-1 (Eli-1) of between about the detection limit and about 3% area as measured by GC method, preferably, of between about the detection limit and about 1% area as measured by GC method, more preferably, of between about the detection limit and about 0.5% area as measured by GC method, and most preferably of between about the detection limit and about 0.2% area as measured by GC method. Also provided is 19TBPO having an amount of 19-TBPO-Eliminate-1 that is less than about 3% area as measured by GC method, preferably less than about 1% area as measured by GC method, more preferably less than about 0.5% area as measured by GC method, or even more preferably less than about 0.2% area as measured by GC method.

Also provided is 19TBPO having an amount of 19-TBPO-Eliminate-2 (Eli-2) of between about the detection limit and about 3% area as measured by GC method, preferably, of between about the detection limit and about 1% area as measured by GC method, more preferably, of between about the detection limit and about 0.5% area as measured by GC method, and most preferably of between about the detection limit and about 0.2% area as measured by GC method. Also provided is 19TBPO having an amount of 19-TBPO-Eliminate-2 that is less than about 3%, preferably less than about 1%, more preferably less than about 0.5%, even more preferably less than about 0.2%.

Also provided is 19TBPO having an amount of Cyclic impurity of between about the detection limit and about 7% area as measured by GC method, preferably, of between about the detection limit and about 6% area as measured by GC method, more preferably, of between about the detection limit and about 3% area as measured by GC method, and most preferably of between about the detection limit and about 2% area as measured by GC method. Also provided is 19TBPO having an amount of Cyclic impurity that is less than about 10%, preferably less than about 7%, more preferably less than about 6%, even more preferably less than about 3%, and most preferably less than about 2%.

Also provided is 19TBPO having an amount of TBDMS-OH (Si—OH) is less than about 3% area as measured by GC method, preferably less than about 2.5% area as measured by GC method, more preferably less than about 2% area as measured by GC method, even more preferably less than about 1% area as measured by GC method, yet even more preferably less than about 0.5% area as measured by GC method, and most preferably less than about 0.2% area as measured by GC method.

Also provided is 19TBPO having an amount of Dimethyl methyl phosphonate (DMMP) of less than about 1%, preferably less than about 0.5%, more preferably less than about 0.2% area as measured by GC method.

Also provided is 19TBPO with an amount of a Methyl tert-butyl 3-hydroxy glutarate (OH-MBSG) of less than about 5%, preferably less than about 2%, more preferably less than about 1% area as measured by GC method.

Also provided is 19TBPO, with an amount of a Methyl tert-butyl 3R-(tert butyl dimethylsilyloxy) glutarate (MBSG) of less than about 2%, preferably less than about 1%, less than about 0.2%.

In another embodiment, the present invention provides 19TBPO, with a 19TBPO-OH less than about 2%, preferably less than about 1%, more preferably less than about 0.5%, or even more preferably less than about 0.2% area as measured by GC method.

In one embodiment, the present invention provides a composition having about 80% to about 90% 19TBPO, preferably about 87% to about 90%, less than about 2% SiOH, less than about 1% DMMP, less than about 1% Eli-1, less than about 1% Eli-2, less than about 1% MSBG, less than about 0.5% OH-19TBPO, less than about 7% of cyclic impurity, as determined by percent area as measured by GC method.

In one embodiment, the purification of 19TBPO-OH is carried out with a thin film evaporator. The use of a thin film evaporator allows a temperature increase during the distillation process without decomposition of 19TBPO, allowing the preparation of pure material. In a typical film evaporator, a feed travels to a rotating distributor plate. The feed can be from the top, which would then fall naturally by gravity onto the plate.

Optional wiper blades, along with centrifugal force resulting from the rotation of the plate then create a thin film by distributing the feed, optimally evenly, over the plate. Due to reduced pressure in the plate chamber and the resulting increase in surface area, the solvent evaporate readily. The remaining product is pushed to the sides by the blades and collected.

The feed is typically in the form of an oil which is obtained by removing the solvent in which 19TBPO is in. The solvent is typically removed in an evaporator, which leaves the oil (without solvent). In principle, in scale-up apparatus, these two operations (evaporation of solvent and then purification of the oil) can be done in the TFE. There can be a first rotating distributor plate one above a second plate and the first and second plates can be heated at different temperatures.

19TBPO is preferably fed into the thin film evaporator, and the evaporation is performed at a temperature of about 130° C. to about 200° C., more preferably of about 150° C. to about 160° C. Preferably, the evaporation is performed under a pressure of about 0 mbar to about 15 mbar, more preferably of about 0.97 mbar to about 1.2 mbar.

Preferably, the 19TBPO obtained by the thin film evaporation method of the invention has a purity of at least about 95%, more preferably of at least about 98%, and even more preferably of at least about 99% area by GC. Preferably, the obtained 19TBPO has an assay purity of at least about 98.4%, more preferably of at least about 99%, and most preferably of at least about 100% w/w.

19TBPO prepared as described above may be converted to rosuvastatin or a pharmaceutically acceptable salt thereof, which are obtained in high purity, due to the high purity of the 19TBPO. The conversion to rosuvastatin or pharmaceutically acceptable salts thereof may be by any method known in the art, e.g. by a Wittig-Horner reaction, as described in U.S.

application Ser. No. 11/543,357 (US Publication 20070167625), incorporated herein by reference.

In another embodiment, the purification is carried out by a combining composition containing 19TBPO with basic and/or oxidizing agents, and then extracting the 19TBPO into an organic phase. This process can comprise combining 19TBPO, and at least one of a base or an oxidizing agent to obtain an aqueous reaction mixture; b) extracting the reaction mixture with a water immiscible organic solvent; and c) recovering 19TBPO from the organic solvent.

The combining can be carried out at a temperature of about 5° C. to about 35° C. The extraction can be carried out at a temperature of about 20° C. to about 40° C.

The base can be an alkali or alkaline earth metal base. Examples of bases include sodium hydroxide, potassium hydroxide, lithium hydroxide, barium hydroxide, potassium carbonate, sodium carbonate, cesium carbonate and lithium carbonate. Preferably the base is sodium hydroxide or sodium carbonate, more preferably sodium hydroxide.

An amount of base is added to obtain a preferred pH of about 10 to about 12, such as about 11.0 to about 11.5. The base can be added dropwise or in one lot to the 19TBPO.

In one embodiment, an oxidizing agent is used. The oxidizing agent can be sodium permanganate, potassium permanganate, calcium permanganate, chromate and dichromate compounds (such as Potassium dichromate, sodium dichromate), osmium tetroxide, Pyridinium chlorochromate and ammonium cerium nitrates. Preferably the oxidizing agent is a permanganate salt such as potassium permanganate.

A combination of a base and an oxidizing agent can also be used. In one embodiment, a combination of permanganate salts as an oxidizing agent, and a base that is a hydroxide or carbonate is used. Preferably a combination of potassium permanganate and sodium hydroxide is used.

The reaction mixture is an aqueous reaction mixture that can be extracted with a water immiscible solvent. Suitable solvents for the reaction mixture include water, which can be present in an aqueous base, and in mixture with solvents miscible with water, such as acetone or a $C_1$-$C_3$ alcohol, preferably methanol. Preferably, when an oxidizing agent is used, only water is used as a solvent. Preferred water to solvent ratio is about 1 to about 5 (v/v).

The solvent used for extraction is a water immiscible solvent so as to obtain two phases. Examples of these solvents include $C_3$-$C_8$ esters, methyl acetate, ethyl acetate, isopropyl acetate, $C_4$-$C_8$ ketones, methyl ethyl ketone, methyl isobutyl ketone, $C_4$-$C_8$ ethers, diethyl ether, isopropyl ether, methyl tert butyl ether, $C_5$ to $C_{12}$ hydrocarbons, toluene, xylene, hexane, cyclohexane, $C_1$-$C_6$ chlorinated solvents dichloromethane, dichloroethane, chloroform, carbon tetrachloride. Preferably the solvent is toluene.

The extraction can be done at basic or acidic pH. When an oxidizing agent is used, particularly a permanganate salt, an acid can be added to quench the reaction mixture. The pH after addition of the acid is preferably about 1 to about 5, preferably about 1 to about 3. Examples of suitable mineral acids include HCl, $H_2SO_4$, and phosphoric acid. Examples of organic acids include acetic aid and formic acid.

After addition of the water immiscible organic solvent, the 19TBPO moves to the organic solvent. The aqueous phase can be further extracted with the water immiscible organic solvent.

The 19TBPO can then be recovered from the water immiscible solvent. The conditions used for recovery may depend on the volatility and the boiling point of the solvent. Preferably the recovery is carried out from about 50° C. below the boiling point to the boiling point of the solvent. Recovery can also be carried out by reducing the pressure, such as a pressure of below one atmosphere or a pressure of below about 100 mm Hg. For example when a hydrocarbon such as toluene is used, recovery can be done by distillation at a temperature of about 50° C. to about 100° C., preferably about 70° C. to about 90° C., and a pressure of less than one atmospheric.

Removing the solvent by distillation also reduces amounts of impurities such as SiOH (such as by removal toluene described above).

The present invention also provides three compounds that are impurities related to 19TBPO. These compounds are: 19TBPO-Eliminate-1 of the following formula:

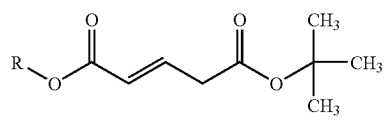

19-TBPO-Eliminate-1 wherein R is methyl, ethyl,

19-TBPO-Eliminate-2 of the following formula:

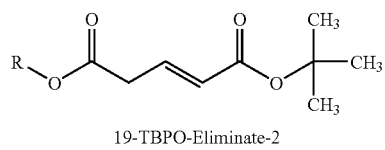

19-TBPO-Eliminate-2 wherein R is methyl, ethyl, and 19-TBPO-Cyclic impurity of the following formula:

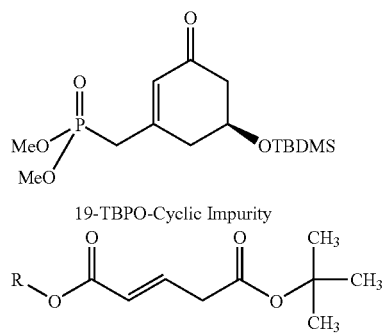

These three compounds can also be provided in their isolated forms. As used herein, the term "isolated" in reference to 19TBPO corresponds to any one of the above impurities that is physically separated from the reaction mixture. For example, the separation can be done by column chromatography.

When R is ethyl, Eliminate-1 has the following NMR:

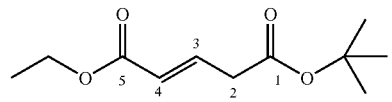

$^1$H NMR (300 MHz, CDCl$_3$): δ 1.28 (t, 3H, CH$_2$—C$\underline{H}_3$), 1.48 (s, 9H, C—(CH$_3$)$_3$), 3.20 (dd, 2H, H$_4$), 4.22 (q, 2H, C$\underline{H}_2$—CH$_3$), 5.90 (d, 1H, H$_2$), 6.90 (m, 1H, H$_3$).

$^{13}$C NMR (75 MHz, CDCl$_3$): δ 14.16 (CH$_2$—$\underline{C}$H$_3$), 28.03 (C—($\underline{C}$H$_3$)$_3$), 38.39 (C4), 60.09 ($\underline{C}$H$_2$—CH$_3$), 81.53 ($\underline{C}$—(CH$_3$)$_3$), 124.44 (C2), 140.41 (C3), 165.14 (C1), 169.10 (C5).

The 19-TBPO-Eliminate 1 can be synthesized substantially free of 19TBPO. In one embodiment, 19-TBPO-Eliminate 1 is obtained having less than about 10% area as measured by GC method 19TBPO. The 19-TBPO-Eliminate 1 may be isolated with column chromatography. Preferably, 19-TBPO-Eliminate 1 is separated from 19TBPO providing a composition of an impurity and 19TBPO containing less than about 10% by area, more preferably, less than about 5% by area, more preferably less than about 1% by area, most preferably, less than about 0.5% by area of 19TBPO, as measured by GC. Preferably, 19-TBPO-Eliminate 1 is present in the composition in an amount of 90% by area or more, more preferably 95% by area or more, more preferably 99% by area or more, and most preferably 99.5% by area or more, as measured by GC.

When R is ethyl, 19-TBPO-Eliminate 2 has the following NMR data:

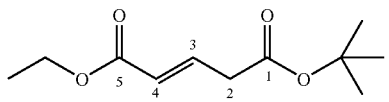

$^1$H NMR (300 MHz, CDCl$_3$): δ 1.29 (t, 3H, CH$_2$—CH$_3$), 1.46 (s, 9H, C—(CH$_3$)$_3$), 3.15 (dd, 2H, H$_4$), 4.15 (q, 2H, CH$_2$—CH$_3$), 5.85 (d, 1H, H$_2$), 7.0 (m, 1H, H$_3$).
$^{13}$C NMR (75 MHz, CDCl$_3$): δ 14.24 (CH$_2$—CH$_3$), 28.10 (C—(CH$_3$)$_3$), 38.73 (C4), 60.39 (CH$_2$—CH$_3$), 81.51 (C—(CH$_3$)$_3$), 124.31 (C2), 140.36 (C3), 165.92 (C1), 170.03 (C5).

The 19-TBPO-Eliminate 2 can be synthesized substantially free of 19TBPO. In one embodiment, 19-TBPO-Eliminate 2 is obtained having less than about 10% area as measured by GC method 19TBPO. The 19-TBPO-Eliminate 2 may be isolated with column chromatography. Preferably, 19-TBPO-Eliminate 2 is separated from 19TBPO providing a composition of an impurity and 19TBPO containing less than about 10% by area, more preferably, less than about 5% by area, more preferably less than about 1% by area, most preferably, less than about 0.5% by area of 19TBPO, as measured by GC. Preferably, 19-TBPO-Eliminate 2 is present in the composition in an amount of 90% by area or more, more preferably 95% by area or more, more preferably 99% by area or more, and most preferably 99.5% by area or more, as measured by GC.

The 19-TBPO-Cyclic impurity has the following NMR and MS data:

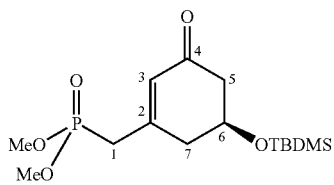

$^1$H NMR (300 MHz, CDCl$_3$): δ 0.07 (s, 3H, Si—CH$_3$), 0.08 (s, 3H, Si—CH$_3$, 0.08 (s, 9H, Si-tBu), 2.52 (m, 1H, H$_5$), 2.71 (m, 1H, H$_5$), 2.44 (m, 1H, H$_7$), 2.61 (m, 1H, H$_7$), 2.79 (m, 2H, H1), 3.78 (s, OMe), 3.77 (s, OMe), 6.00 (d, H$_3$).
$^{13}$C NMR (75 MHz, CDCl$_3$): δ −4.74 (Si—CH$_3$), 25.79 (Si—C(CH$_3$)$_3$), 25.79 (Si—C(CH$_3$)$_3$), 35.32 (C1), 40.13 (C5), 46.84 (C7), 53.14 (OMe), 67.35 (C6), 127.69 (C3), 152.09 (C2), 197.84 (C4).
$^{31}$P NMR: δ 26.54.
MS (DCI+) MH+: 349

The 19-TBPO-cyclic impurity can be synthesized substantially free of 19TBPO. In one embodiment, 19-TBPO-cyclic impurity is obtained having less than about 10% area as measured by GC method 19TBPO. The 19-TBPO cyclic impurity may be isolated with column chromatography. Preferably, 19-TBPO-cyclic impurity is separated from 19TBPO providing a composition of an impurity and 19TBPO containing less than about 10% by area, more preferably, less than about 5% by area, more preferably less than about 1% by area, most preferably, less than about 0.5% by area of 19TBPO, as measured by GC. Preferably, 19-TBPO-cyclic impurity is present in the composition in an amount of 90% by area or more, more preferably 95% by area or more, more preferably 99% by area or more and most preferably 99.5% by area or more, as measured by GC.

The compounds 19-TBPO-Eliminate 1 and 19-TBPO-Eliminate-2 can be prepared by combining a solvent and a base at a temperature of about −10° to about −100° C. with dimethyl methyl phosphonate to obtain a salt, and; adding methyl tert-butyl (3) R dimethylsilyloxy glutarate to the salt to obtain 19-TBPO Eliminate 1 and 19-TBPO Eliminate 2 as a mixture. To accelerate the reaction, the reaction mixture can be stirred, such as at a temperature range of about −45° C. to about −75° C.

Preferably, the base is capable of forming a carbon anion. The base may be selected from the group consisting of: $C_1$-$C_6$ alkyl lithium, alkali metal hydrides, and alkali metal amides. More preferably, the base is alkyl lithium or n-butyl lithium in hexane. The carbon anion formation is preferably carried out under inert conditions such as nitrogen, helium or argon atmosphere. Also, the conditions are preferably anhydrous, so that there is less than about 0.1% by weight water in the reaction mixture. Hexamethyldisilazane can also be optionally added to the reaction mixture.

After the reaction, the temperature can be raised such as to about −10 to about 30° C. A quenching reagent such as ammonium chloride, water, an acid such as HCl or acetic acid, or a combination thereof, can be added. In one embodiment, the reaction mixture is quenched so to obtain an aqueous acidic reaction mixture having a pH of about 1 to about 5, such as about 2. A water immiscible organic solvent such as ethyl acetate or toluene or MIBK (methyl isbutyl ketone) is then added. The temperature can further be raised to room temperature at this point. After layer separation, the water immiscible solvent can be washed with water or a salt solution such as a sodium chloride solution. The mixture of 19-TBPO-Eliminate 1 and 19-TBPO-Eliminate-2 can be recovered as an oil by removing the solvent, such as under a pressure of less than one atmosphere, preferably a pressure of less than 100 mmHg. 19-TBPO-Eliminate 1 and 19-TBPO-Eliminate-2 can further be separated from each other by chromatography.

Removing the solvent by distillation also reduces amounts of impurities such as SIOH, such as by removing under one atmosphere, preferably less than 100 mmHg.

Also provides is a process for preparing 19-TBPO cyclic impurity, comprising the steps of:
 a) preparing a mixture of a solvent and dimethylmethyl phosphonate at a temperature of about −10° C. to about −100° C. to achieve a reaction mixture;
 b) combining base with the reaction mixture to obtain a salt;
 c) adding diethyl tert-butyldimethylsilyloxy glutarate to achieve the Cyclic Impurity;
 d) recovering the cyclic impurity.

The solvent and dimethylmethyl phosphonate can be combined at RT, such as temperature of about 15° C. to about 30° C., and then cooled. Preferably the base is capable of forming a carbon anion. The base may be $C_1$-$C_6$ alkyl lithium, alkali metal hydrides, alkali metal amides. More preferably, the base is alkyl lithium or n-butyl lithium in hexane. The carbon anion formation is preferably carried out under inert conditions such as nitrogen, helium or argon atmosphere. Also the conditions are preferably anhydrous, so that there is less than about 0.1% by weight water in the reaction mixture. Hexamethyldisilazane can also be optionally added to the reaction mixture.

After the reaction, the temperature can be raised such as to about −10° C. to about 30° C. A quenching reagent such as ammonium chloride, water, an acid such as HCl or acetic acid, or a combination thereof, can be added. In one embodiment, the reaction mixture is quenched so to obtain an aqueous acidic reaction mixture having a pH of about 1 to about 5, such as about 2. A water immiscible organic solvent such as ethyl acetate or toluene or MIBK is then added. The temperature can further be raised to room temperature at this point. After layer separation, the ethyl acetate can be washed with water or a salt solution such as a sodium chloride solution. The cyclic impurity can be recovered as an oil by removing the solvent, such as under a pressure of less than one atmosphere, preferably a pressure of less than 100 mmHg.

19-TBPO-Eliminate 1 and 19-TBPO-Eliminate-2 and 19-TBPO-Cyclic Impurity may be used as reference markers and reference standards in determining their presence and amount in a sample of 19TBPO or impurities.

In one embodiment, the invention encompasses a process of determining the presence of an impurity in 19TBPO by a process comprising carrying out GC with the impurity as a reference marker, wherein the impurity is either 19-TBPO-Eliminate1, 19-TBPO-Eliminate-2 and 19-TBPO-Cyclic Impurity.

Preferably, the method comprises (a) measuring by GC the relative retention time (referred to as RRT, or RRF, respectively) corresponding to the impurity in a reference marker sample; (b) determining by GC the relative retention time corresponding to the impurity in a sample comprising the impurity and 19TBPO; and (c) determining the relative retention time of the impurity in the sample by comparing the relative retention time (RRT or RRF) of step (a) to the RRT or RRF of step (b), wherein the impurity is either 19-TBPO-Eliminate 1, 19-TBPO-Eliminate-2 and 19-TBPO-Cyclic Impurity.

In another embodiment, the present invention encompasses a process of determining the amount of an impurity in 19TBPO by a process comprising carrying out GC with the impurity as a reference standard, wherein the impurity is either 19-TBPO-Eliminate 1, 19-TBPO-Eliminate-2 and 19-TBPO-Cyclic Impurity.

Preferably, the above process comprises: (a) measuring by GC the area under a peak corresponding to the impurity in a reference standard comprising a known amount of the impurity; (b) measuring by GC the area under a peak corresponding to impurity in a sample comprising the impurity and 19TBPO; and (c) determining the amount of the impurity in the sample by comparing the area of step (a) to the area of step (b).

In yet another embodiment, the present invention provides a GC method for determining the purity of 19TBPO, said method comprising the steps of:

(a) combining 19TBPO with acetonitrile to obtain a solution;

(b) injecting the solution into (50%-phenyl)-methylpolysiloxane, 30 m×0.53 mm×1.0 μm film thickness, column;

(c) eluting the sample from the column at about using He as carrier gas;

(d) measuring the impurity content, such as with a Flame Ionisation detector.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Instrumental

Wiped Film Evaporator Made by Pope.
0.02 m2 heat transfer area, 50 mm diameter, made in glass with three Teflon wipers GC Method:

Standard Solution Preparation
Weigh accurately 20 mg of 19TBPO standard into 10 ml volumetric flask, dissolve, and bring to volume with Diluent.

Sample Solution Preparation
Weigh accurately 20 mg of 19TBPO sample into 10 ml volumetric flask, dissolve, and bring to volume with Diluent.

Procedure
Inject the standard and sample solutions continuing the chromatogram up to the end of gradient.

Gas Chromatography Impurity Profile of 19TBPO

Instrument

Gas Chromatograph equipped with Flame Ionisation Detector.

Column
DB 17, 30 m×0.53 mm×1.0 μm film thickness, Agilent C/N: 125-1732 or equivalent.

| Chromatographic Conditions | |
| --- | --- |
| a.) Initial oven temperature | 40° C. |
| b.) Initial hold time | 3.0 minute |
| c.) Initial-1 ramp rate | 20° C./minute |
| d.) Intermediate-1 oven temperature | 160° C. |
| e.) Intermediate-1 hold time | 10.0 minute |
| f.) Initial-2 ramp rate | 10° C./minute |
| g.) Intermediate-2 oven temperature | 210° C. |
| Column & Packing: | DB-17 30 m × 0.53 mm 1 μm film thickness |
| Injector temperature | 180° C. |
| Detector temperature | 300° C. |
| Oven temperature | 40° C. for 3 minutes, then 20° C./minute up to 160° C., then 160° C. for 10 minutes, then 10° C./minute up to 210° C., then 210° C. for 10 minutes, then 20° C./minute up to 270° C. for 10 minutes. |
| Injection volume | 1.0 μl |
| Flow | 10 ml/min Helium at 40° C. |
| Mode | Constant flow |
| Split ratio | 1:10 |
| Detector | FID |
| Diluent | Acetonitrile |
| h.) Intermediate-2 hold time | 10.0 minute |
| i.) Final ramp rate | 20° C./minute |
| j.) Final oven temperature | 270° C. |
| k.) Final hold time | 10.0 minute |
| l.) Injector temperature | 180° C. |
| m.) Detector temperature | 300° C. |
| n.) Carrier gas (He) flow | 10.0 ml/min |
| o.) Mode | Constant flow |
| p.) Injection volume | 1.0 μl |
| q.) Split ratio | Splitless |

Temperature and flow rate may be varied in order to achieve the required system suitability.

Diluent
Acetonitrile
TBDMSiOH: 3.48 minutes
DMMP: 5.82 minutes
Eli-2: 8.80 minutes
Eli 1: 9.00 minutes
Cyclic Impurity: 31.7 minutes
ELI-1 and ELI-2 in all GC analysis provided below have R as methyl group.

Example 1

Stability of 19TBPO Under Variable Temperatures

The thermal stability of 19TBPO was tested by heating the product in the range 100-180° C. under atmospheric pressure of nitrogen for 4 hours.
The results are presented in the following table:

|  | Temperature ° C. | Assay % (HPLC) | TBDMSiOH % (GC) |
|---|---|---|---|
| Starting 19TBPO |  | 52.3 | 15.6 |
| 1 | 50 | 53.2 | 14.5 |
| 2 | 100 | 56.5 | 6.8 |
| 3 | 120 | 47.2 | 17.8 |
| 4 | 150 | 6.4 (after 2 h) | 13.8 |
| 5 | 180 | 0 (after 2 h) | 61.6 |

At temperatures above 100° C., the assay decreased with the increase of temperature.
The level of the impurity TBDMSiOH decreases at a temperature under 100° C., and increases with the increase of temperature beyond 100° C.

Example 2

Purification of 19TBPO by TFE 26 g 19TBPO residue (TN4259, purity GC 63.4%) was purified by thin film evaporator (TFE) at 150° C. under 1.2 mbar vacuum to obtain 11.6 g 19TBPO (Purity GC 95.5% area; assay 98.4% w/w).

Example 3

Purification of 19TBPO by TFE 33 g 19TBPO residue (TN4262, purity GC 70.4%) was purified by thin film evaporator (TFE) at 160° C. under 0.97 mbar vacuum to obtain 16.6 g 19TBPO (Purity GC 98.4% area; assay 100% w/w).

Example 4

Preparation of 19TBPO According to WO 03/087112

A 250 mL flask washed with dry nitrogen was charged with THF (42 mL) and cooled to −10° C. DMMP (9.32 g) was added while stirring and the solution was cooled to −78° C. BuLi (1.6M in Hexanes, 44.2 mL) was added dropwise, so that the temperature did not exceed −73° C. and the mixture was stirred at −75° C. for 3 h. MBSG (10 g) was added dropwise at −75° C. and the mixture was slowly warmed to 0° C. during 6 h. Water (40 mL) was added and the reaction mixture was neutralized with 5% HCl. The product was extracted with EtOAc (40 mL). The organic fraction was dried over MgSO₄ and the solvent was evaporated under reduced pressure giving 11.08 g of crude 19TBPO (Assay 71.4%, Yield 62%).

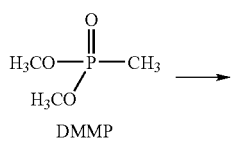

DMMP

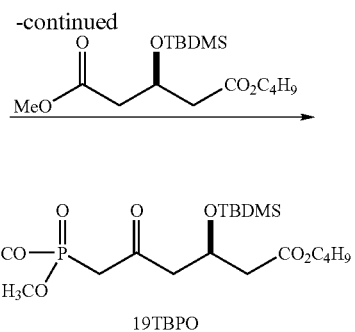

DMMP is commercially available.

Example 5

Preparation of 19TBPO in Accordance to the Co-Pending application Ser. No. 12/148,535

Preparation of t-butyl (3R)-3-(t-butyl dimethylsilyloxy)-6-dimethoxyphosphinyl-5-oxohexante(19TBPO) from t-butyl methyl (3R)-3-(t-butyl dimethylsilyloxy)-glutarate (MBSG (Formula-(III)))

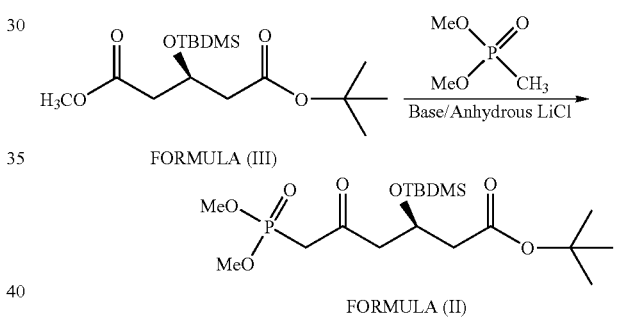

To four neck round bottom flask under nitrogen atmosphere was added 209.8 gm dimethyl methylphosphonate, 900.0 ml lithium chloride solution (36.0 gm anhydrous lithium chloride was dissolved in 900 ml Dry Tetrahydrofuran at 50° C.) and 350 ml dry tetrahydrofuran at room temperature Cooled reaction mass up to −80° C. to −78 and added 1313 ml 1.0 M n-Butyllithium in hexane solution (820 ml 1.6M n-butyllithium in hexane was diluted with 493 ml hexane under nitrogen atmosphere) to reaction mass over the period of 30-40 minutes at −80 to −78° C. Stirred reaction mass for 30 minutes at −80 to −78° C. for anion formation. Added drop wise 125 gm MBSG (formula-III) with 1250 ml dry tetrahydrofuran at −80 to −78° C. over the period of 100 to 110 minutes. After completion of addition, stirred reaction mass for 30 minutes and reaction was monitored by GC and added 1250 ml of 6.72% ammonium chloride solution at −78 to −65° C. Cooled reaction mass up to room temperature. Adjust pH 1.5 using 1N hydrochloric acid solutions at RT. Added 625 ml toluene and stirred for 15-20 minutes. Layers separated and organic layer was washed twice with 1250 ml DM water followed by 1250 ml saturated sodium chloride solution. Organic layer was concentrated under vacuum up to dryness to get pale yellow colored transparent product 126.04 gm, assay 8301%, purity 75.58% (by GC % Area) and yield 65.95%.

Impurity Profile:

| | Impurities(% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| 1 | 3.48 | .04 | 5.89 | 5.123 | NIL | 0.8 | 0.04 | 73.58 | 2.8 |

ABBREVIATIONS

Si—OH: Silanol

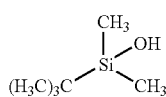

DMMP: Dimethyl methylphosphonate

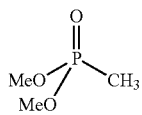

19TBPO Elimination impurity-1

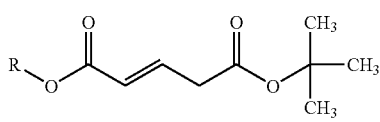

Wherein R is Methyl, Ethyl

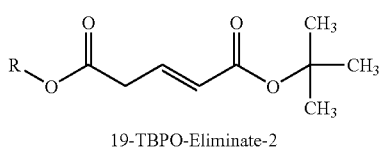

Wherein R is Methyl, Ethyl
OH-MBSG: Hydroxy MBSG

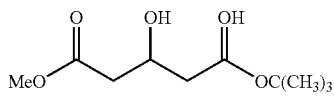

MBSG: MBSG (starting material)
19TBPO-OH: Hydroxy 19TBPO

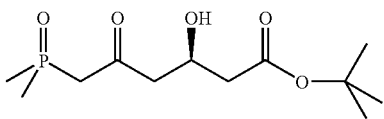

19TBPO: 19TBPO (product)
Cyclic: Cyclic Impurity

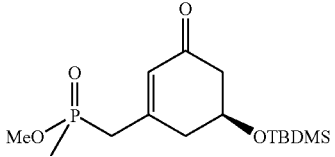

Example 6

Purification of 19TBPO by Chemical Method

To four neck round bottom flask, added 10.0 gm 19TBPO having purity: 73.62% assay 83.9% by GC, 30 ml methanol, 10 ml DM water and added sodium hydroxide solution (0.44 gm sodium hydroxide was dissolved in 20 ml DM water at room temperature) drop wise to adjust pH to 11.2 and stirred at 35-45° C. and maintain pH at 11.0 by constant addition of Sodium hydroxide solution. Added toluene 100 ml and stirred for 15 minutes and layer was separated and aqueous layer was back extracted with 50 ml toluene and combined with former organic layer and combined organic layer was concentrated under vacuum to get pale yellow coloured transparent of product, 19TBPO 8.2 gm, assay 88.06%, purity 84.65% (by GC Area) yield 86.0% (content basis by GC).

Example 6.1

Impurity Profile

| | Impurities (% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| Before Purification | 2.23 | 0.2 | 6.56 | 5.14 | 3.66 | Nil | 0.86 | 73.62 | 1.98 |
| After Purification | 2.22 | 0.07 | 2.74 | 2.45 | 4.49 | Nil | 1.00 | 84.65 | 0.14 |

Example 6.2

Impurity Profile

| | Impurities (% by GC) | | | | | | | | |
|---|---|---|---|---|---|---|---|---|---|
| | Si—OH | DMMP | Eli-1 | Eli-2 | OH-MBSG | MBSG | -19TBPO-OH | 19TBPO | Cyclic |
| Before Purification | 2.23 | 0.2 | 6.56 | 5.14 | 3.66 | Nil | 0.86 | 73.62 | 1.98 |
| After Purification | 2.22 | 0.07 | 1.1 | 0.9 | 4.49 | Nil | 1.00 | 87.50 | 0.14 |

Example 7

Purification of 19TBPO by Chemical Method

Purification of 19TBPO (Formula (II)):

To four neck round bottom flask, added 25.0 gm 19TBPO having purity: 71.23% by GC, 100 ml De-mineralized water at room temperature. Added solution of mixture of 2.81 gm potassium permanganate and 1.90 gm sodium carbonate dissolved in 465 ml De-mineralized water, at 5-10° C. and stirred at 5-10° C. for 5 hours. Quenched the mass with diluted hydrochloric acid and adjusted mass pH to 1.5 and added toluene 250 ml and filtered through celite bed. At this point optionally, the reaction mixture can be stirred with dilute HCl solution in presence of toluene. Washed the bed with 25 ml toluene and the organic layers was separated and aqueous layer was extracted for several times with 125 ml toluene combined with former organic layer and organic layer was washed twice with 250 ml DM Water followed by brine wash and then organic layer was concentrated under reduced pressure to obtain dark brown oily product of 19TBPO (formula (II)), 8.2 gm, assay 93.73%, purity 84.66% (by GC Area) yield 95.73% (content basis by GC).

Example 7.1

Impurity Profile

| | Impurities (% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| Before Purification | 2.01 | 0.2 | 6.49 | 5.66 | 0.13 | 0.41 | 1.45 | 71.23 | 7.35 |
| After Purification | 1.57 | 0.16 | 1.73 | 1.56 | 0.22 | 0.22 | 0.1 | 84.66 | 5.65 |

Example 7.2

Impurity Profile

| | Impurities (% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| Before Purification | 2.01 | 0.2 | 6.49 | 5.66 | 0.13 | 0.41 | 1.45 | 71.23 | 7.35 |
| After Purification | 1.57 | 0.16 | 0.8 | 0.75 | 0.22 | 0.22 | 0.1 | 87.8 | 5.65 |

Example 8

Purification of 19TBPO by TFE

To Wiped Film Evaporator made by Pope, 0.02 meters square heat transfer area, 50 mm diameter, made in glass with three Teflon wipers. Performed the Thin film evaporation at 160° C. to obtain pale yellow to yellow oily product of formula (I), yield: 97.0% (Content basis by GC), assay: 81.7%, purity: 88.9% (by GC Area Impurity Purity:

| | Impurities (% by GC) | | | | | | | | |
|---|---|---|---|---|---|---|---|---|---|
| | SiOH | DMMP | Eli-1 | Eli-2 | OH-MBSG | MBSG | 19TBPO-OH | 19TBPO | Cyclic |
| Before Purification | 3.4 | Nil | 4.2 | 3.7 | 0.64 | 0.46 | 0.64 | 75.3 | 5.6 |
| After Purification | Nil | Nil | 0.18 | 0.18 | Nil | Nil | 0.48 | 88.9 | 7.0 |

Example 9

Preparation of 19TBPO

Preparation of t-butyl (3R)-3-(t-butyl dimethylsilyloxy)-6-dimethoxyphosphinyl-5-oxohexante (19TBPO) from t-butyl methyl (3R)-3-(t-butyl dimethylsilyloxy)-glutarate (MBSG, Formula-(III)).

To four neck round bottom flask under nitrogen atmosphere added 16.78 gm dimethyl methylphosphonate and 100 ml dry tetrahydrofuran at room temperature. Cooled reaction mass up to −80° C. to −78 and added 105 ml 1.0 M n-Butyl-lithium in hexane solution (66 ml 1.6M n-butyllithium in hexane was diluted with 39 ml hexane under nitrogen atmosphere) to reaction mass over the period of 30-35 minutes at −80 to −78° C. Stirred reaction mass for 90 minutes at −80 to −78° C. for anion formation. Added drop wise 10 gm formula-II with 100 ml dry tetrahydrofuran at −80 to −78° C. over the period of 100 to 110 minutes After completion of addition, stirred reaction mass for 30 minutes and reaction was monitored by GC and added 100 ml of 6.72% ammonium chloride solution at −78 to −65° C. Raised reaction mass temperature up to room temperature. Adjust PH 1.5 using 1N hydrochloric acid solution at RT. Added 50 ml toluene and stirred. For 15-20 minutes. Layer was separated and organic layer was washed with twice time 100 ml DM water followed by 100 ml saturated sodium chloride solution. Organic layer was concentrated under vacuum up to dryness to get pale yellow coloured transparent product 10.5 gm, assay 55.5%, purity 51.71% (by GC % Area) and yield 45.82%.

Impurity Profile

| | Impurities(% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| 1 | 9.85 | 0.07 | 7.86 | 7.24 | 0.12 | 1.13 | 2.91 | 51.71 | 9.23 | a) Purification of 19TBPO (Formula (II)):

To four neck round bottom flask, added 10.5 gm 19TBPO having purity: 51.5%, assay 55.5% by G.C, at room temperature. Added solution of mixture of 1.95 gm potassium permanganate and 0.35 sodium hydroxide gm dissolved in 200 ml De-mineralized water, at 5-10° C. and stirred at 5-10° C. for 5 hours. Quenched the mass with diluted hydrochloric acid and adjusted mass pH to 2-3 and added toluene 55 ml and filtered through celite bed and washed the bed with 10.5 ml toluene and the organic layers was separated and aqueous layer was back extracted with 27.5 ml toluene, combined with former organic layer and organic layer were washed with twice time 55 ml DM Water followed by brine wash and organic layer was concentrated under reduced pressure to obtain dark brown oily product of 19TBPO (formula (II)) 5.2 gm, assay 71.2%, purity 85.83% (by GC Area) yield 67.28% (content basis by GC).

Impurity Profile:

| | Impurities(% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| Before Purification | 9.85 | 0.07 | 7.86 | 7.24 | 0.12 | 1.13 | 2.91 | 51.71 | 9.23 |
| After Purification | 1.74 | Nil | 0.11 | 0.10 | Nil | 1.81 | Nil | 85.83 | 4.92 | b) Purification of 19TBPO (Formula (II)):

To four neck round bottom flask, added 168.0 gms 19TBPO (formula (II)) having purity: 66.70%, assay 68.4% by G.C, at room temperature. Added solution of mixture of 28.88 gms potassium permanganate and 4.75 gm sodium hydroxide dissolved in 2000 ml DM water, at 20-30° C. and stirred for 8-15 hours. Quenched the mass with diluted hydrochloric acid and adjusted mass pH to 4.0-5.0 and added toluene 67.5 ml and filter the mass over Hyflo. Wash the Hyflo with toluene 500 ml and add sodium chloride to it. Stir and then separate layers. Extract the aqueous layer. Wash the toluene layer with sodium chloride solution 2×500 ml. Organic layer is concentrated under reduced pressure to obtain dark browny oily product (135.0 g), purity 88.58%, Assay 88.2%.

Impurity Profile:

| | Impurities(% by GC) | | | | | | | | |
|---|---|---|---|---|---|---|---|---|---|
| | Si—OH | DMMP | Eli-1 | Eli-2 | OH-MBSG | MBSG | 19TBPO-OH | 19TBPO | Cyclic |
| Before Purification | 3.48 | Nil | 7.14 | 6.37 | Nil | 0.13 | 1.19 | 66.7 | 3.94 |
| After Purification | 0.30.- | — | — | — | — | 0.1 | 0.12 | 88.86 | 1.37 |

Example 10

Process for Preparation of Cyclic Impurity Under Anhydrous Conditions and Nitrogen Atmosphere To 210 ml THF added dimethylmethyl phosphonate 87.4 g at 20-25° C. and cool to −80 to −85° C. Added n-butyl lithium solution in hexane (1.6 molar) (386 ml at −80 to −85° C. Stirred for 2 Hrs at −80 to −85° C. Added a solution of Diethyl tert-butyldimethylsilyloxy glutarate (PHDEG) 42.0 g in 210 ml THF) in 1 Hr at −80 to −85° C. Stir for 2 Hrs at −80 to −85° C. Slowly raise temperature to 0° C. in 3 Hrs and add 20% ammonium chloride solution 85 ml at 0 to 5° C. Adjust pH to 2.0 with 2N Hydrochloric acid solution (160 ml) at 0 to 5° C. and add ethyl acetate (200 ml). Raise temperature to 20-25° C. and stir for 15 minutes. Settle and separate the layers.

Keep upper organic layer separate and extract the lower aq. Layer with ethyl acetate (200 ml). After layer separation combine the ethyl acetate layers and wash with 28% sodium chloride solution 420 ml.

Separate layers and concentrate the upper ethyl acetate layer completely under vacuum to get cyclic impurity as oil.

Yield: 30 gms; GC Purity: 50.38% of the cyclic compound

Purification of Cyclic Impurity

Cyclic impurity (Crude) 50.38% by GC is purified by column chromatography using silica gel as the stationary phase and mixture of hexane and ethyl acetate as eluent. The cyclic impurity so obtained is 79.77% area by GC.

Example 11

Preparation of E1 and E2 Impurities

Under anhydrous conditions and Nitrogen atmosphere, to 140 ml THF add Hexamethyldisilazane (freshly distilled) 32.3 gm at RT. Cool to −50° C. and add n-butyl lithium solution in hexane (1.6 molar) (125 ml) at −53 to −49° C. Stir for 15-20 minutes at −50° C. and add dimethyl methyl phosphonate (13.64 gm) at −50 to −52° C. Stir for 30 to 35 minutes and cool to −70° C. and stir for further 30 minute. Added methyl tert-butyl (3)R dimethylsilyloxy glutarate (MBSG) at −71 to −68° C. & stir at −70° C. for 30 minutes. Quench the reaction by adding to the reaction mass a mixture of 30 ml Acetic acid in 30 ml THF at −70° C. Add DM water 100 ml at −70 to −65° C. and toluene 100 ml and raise temperature to 20° C. Stir and separate layers. Wash upper organic layer with 5% acetic acid 300 ml followed by 1N hydrochloric acid 300 ml. Distill off the organic layer completely under vacuum to get E1 and E2 oil impurities.

Yield: 22.0 gm; Purity by GC: 37.1% (E1) 50.8% (E2).

What is claimed is:

1. A process for purifying t-butyl (3R)-3-(t-butyldimethylsilyloxy)-6-dimethoxyphosphinyl-5-oxohexanoate (19TBPO) comprising combining a composition containing 19TBPO with basic and/or oxidizing agents, and then extracting the 19TBPO into a water immiscible organic solvent.

2. The process of claim 1, wherein the process comprises combining 19TBPO and at least one of a basic agent or an oxidizing agent to obtain an aqueous mixture; b) extracting the reaction mixture with a water immiscible organic solvent; and c) recovering 19TBPO from the organic solvent.

3. The process of claim 1, wherein combining can be carried out at a temperature of about 5° C.-35° C.

4. The process of claim 1, wherein extraction can be carried out at a temperature of about 20° C. to about 40° C.

5. The process of claim 1, wherein the basic agent is a alkali or alkaline earth metal base.

6. The process of claim 5, wherein the basic agent is sodium hydroxide, potassium hydroxide, lithium hydroxide, barium hydroxide, potassium carbonate, sodium carbonate, cesium carbonate and lithium carbonate.

7. The process of claim 6, wherein the basic agent is sodium hydroxide or sodium carbonate.

8. The process of claim 1, wherein an amount of the basic agent is added to obtain a preferred pH of about 10 to about 12.

9. The process of claim 1, wherein an oxidizing agent is used.

10. The process of claim 1, wherein the oxidizing agent is sodium permanganate, potassium permanganate, calcium permanganate, chromate compounds, dichromate and osmium tetroxide, Pyridinium chlorochromate or ammonium cerium nitrates.

11. The process of claim 1, wherein the oxidizing agent is a permanganate salt.

12. The process of claim 1, wherein a combination of a basic agent and an oxidizing agent is used.

13. The process of claim 1, wherein a combination of permanganate salts as an oxidizing agent, and a base selected from a hydroxide or carbonate is used.

14. The process of claim 13, wherein a combination of potassium permanganate and sodium hydroxide is used.

15. The process of claim 2, wherein a solvent for the reaction mixture is water, a mixture of acetone and water or a mixture of a $C_1$-$C_3$ alcohol and water.

16. The process of claim 15, wherein the $C_1$-$C_3$ alcohol is methanol.

17. The process of claim 2, wherein an oxidizing agent is used and the solvent for the aqueous mixture is water.

18. The process of claim 1, wherein the solvent used for extraction is selected from the group consisting of a $C_3$-$C_8$ ester, a $C_4$-$C_8$ ketone, a $C_4$-$C_8$ ethers, a $C_5$-$C_{12}$ hydrocarbon, a $C_1$-$C_6$ chlorinated solvent.

19. The process of claim 18, wherein the $C_3$-$C_8$ ester is methyl acetate, ethyl acetate, or isopropyl acetate, the $C_4$-$C_8$ ketone is methyl ethyl ketone, or methyl isobutyol ketone, the $C_4$-$C_8$ ether is diethyl ether, isopropyl ether, or methyl tert butyl ether, the $C_5$-$C_{12}$ hydrocarbon is toluene, xylene, hexane, or cyclohexane, and the $C_1$-$C_6$ chlorinated solvent is dichloromethane, dichloroethane, chloroform, or carbon tetrachloride.

20. The process of claim 19, wherein the solvent is toluene.

21. The process of claim 1, wherein an acid is added before extraction to obtain a pH about 1 to about 5.

22. The process of claim 21, wherein the acid is a mineral acid.

23. The process of claim 22, wherein the mineral acid is HCl, $H_2SO_4$, or phosphoric acid.

24. The process of claim 21, wherein the acid is an organic acid.

25. The process of claim 24, wherein the organic acid is acetic aid or formic acid.

26. The process of claim 1, wherein the 19TBPO is recovered from the water immiscible solvent.

27. The process of claim 26, wherein recovery is carried out at a temperature from about 50° C. below the boiling point to the boiling point of the solvent.

28. The process of claim 26, wherein recovery is carried out by reducing the pressure, such as a pressure of below one atmosphere or a pressure of below about 100 mm Hg.

29. The process of claim 26, wherein recovering reduces the amount of impurity SiOH.

30. The process of claim 10, wherein the dichromate compound is potassium dichromate or sodium dichromate.

31. The process of claim 11, wherein the permanganate salt is potassium permanganate.

* * * * *